(12) United States Patent
Nance et al.

(10) Patent No.: US 7,392,856 B2
(45) Date of Patent: Jul. 1, 2008

(54) ROTATING DRUM VARIABLE DEPTH SAMPLER

(75) Inventors: Thomas A. Nance, Aiken, SC (US); Timothy J. Steeper, Trenton, SC (US)

(73) Assignee: Washington Savannah River Company, LLC, Aiken, SC (US)

( * ) Notice: Subject to any disclaimer, the term of this patent is extended or adjusted under 35 U.S.C. 154(b) by 167 days.

(21) Appl. No.: 11/341,107

(22) Filed: Jan. 27, 2006

(65) Prior Publication Data

US 2006/0175089 A1 Aug. 10, 2006

(51) Int. Cl.
*E21B 25/10* (2006.01)

(52) U.S. Cl. ............... 175/20; 175/58; 175/252; 73/864.44

(58) Field of Classification Search ........... 175/20, 175/58, 244, 245, 249, 252; 172/22; 73/864.44
See application file for complete search history.

(56) References Cited

U.S. PATENT DOCUMENTS

| 2,057,142 | A | * | 10/1936 | Fry ............... 172/22 |
|---|---|---|---|---|
| 3,383,131 | A | * | 5/1968 | Rosfelder ............. 294/68.21 |
| 3,978,932 | A | | 9/1976 | Mielke |
| 4,096,749 | A | | 6/1978 | Stewart |
| 4,376,392 | A | | 3/1983 | Beitel |
| 4,498,547 | A | * | 2/1985 | Herkness, II .............. 175/244 |
| 5,474,141 | A | | 12/1995 | Hart |
| 5,492,021 | A | | 2/1996 | Bourgeois et al. |
| 5,494,119 | A | | 2/1996 | Tully |
| 5,831,185 | A | | 11/1998 | Maxwell et al. |
| 6,098,724 | A | * | 8/2000 | Ricker ............... 175/20 |
| RE37,066 | E | | 2/2001 | Casey et al. |

* cited by examiner

*Primary Examiner*—Jennifer H. Gay
*Assistant Examiner*—Robert E Fuller
(74) *Attorney, Agent, or Firm*—J. Herbert O'Toole; Nexsen Pruet, LLC

(57) ABSTRACT

A sampling device for collecting depth-specific samples in silt, sludge and granular media has three chambers separated by a pair of iris valves. Rotation of the middle chamber closes the valves and isolates a sample in a middle chamber.

5 Claims, 3 Drawing Sheets

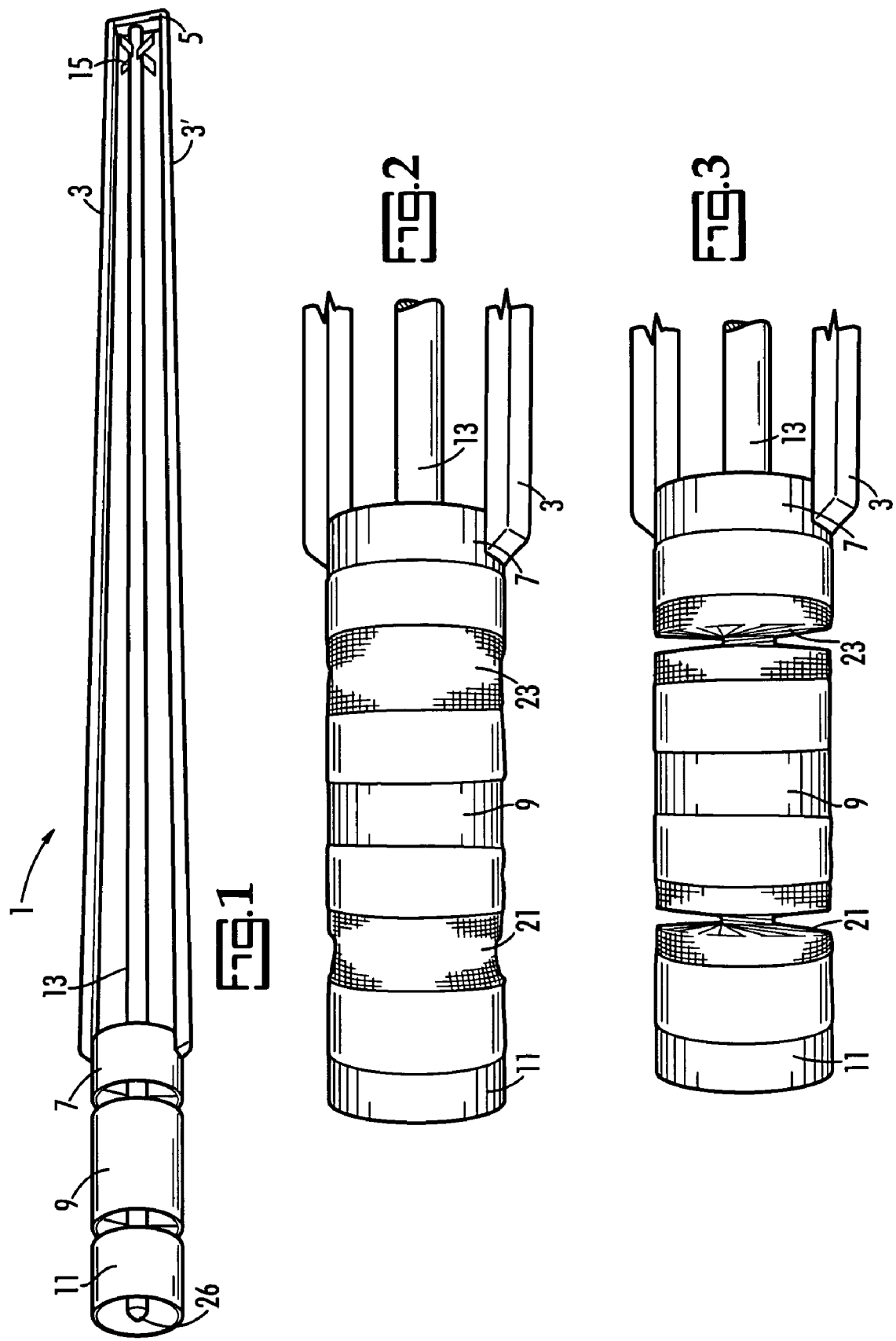

ROTATING DRUM VARIABLE DEPTH SAMPLER

STATEMENT OF U.S. GOVERNMENT RIGHTS

This invention was made with Government support under Contract Number DE-AC09-96SR18500 between Washington Savannah River Company and the United States Department of Energy. The U.S. Government has certain rights in this invention.

BACKGROUND OF THE INVENTION

Accurate analyses of samples, regardless of the source, begins with the method for collecting the sample. Core samples of soils and sludges must be reliable, accurate, and reproducible in determination of the depth at which a sample was taken and must minimize contamination by soils and sludges at different depths. Numerous devices have been reported.

U.S. Pat. No. 3,978,932 to Mielke discloses a core sampler for soils characterized by a resilient retaining ring beneath a liner. U.S. Pat. No. 5,831,185 to Maxwell et al. discloses a pneumatically driven core sample having a trap door to retain the sample.

U.S. Pat. No. 4,376,392 to Beitel discloses a pneumatic sludge sampler. U.S. Pat. No. 5,474,141 to Hart discloses a chisel shaped core sampler with a trap door collection system. U.S. Pat. No. 5,492,021 to Bourgeoise et al. discloses a core sampler for hard surfaces based upon a hole saw.

U.S. Pat. No. 5,494,119 discloses a pneumatic core sampler with a split spoon collector. U.S. Pat. No. 4,096,749 to Stewart discloses a double-walled core sampler for testing wet concrete. U.S. Pat. No. RE 37,066 to Casey et al. is directed to a soil sampler with multiple removable liners for collection at different depths.

Common commercial samplers are available from vendors such as Enviroquip, Fisher Scientific, Kahl Scientific Instrument Corp., AMS Inc., and Advanced Concepts and Designs, Inc.

Core samplers for soils require a driving system, often pneumatic. Samplers for silts, sludge, other semi-plastic materials and granular or comminuted material may be hand operated. Accuracy of depth of the collected sample becomes critical, especially with rivers, lakes and ponds, storage tanks, and other soft materials which have been serially loaded with (different) contaminants and/or have been mixed before analytical processing. Improved, easier to operate, accurate sludge samplers always are in demand.

BRIEF DESCRIPTION OF THE INVENTION

It is a first objective of the invention to provide a sampler for sludge, silt and granular solids which securely captures at least a qualitative and preferably a quantitative sample at a pre-selected depth. It is a second objective of the invention to provide a sampler that can be readily manipulated by one person through a small opening such as a drum bung hole. It is a third objective of the invention to provide a sampler which does not require the availability of electricity or other power sources. This is important when analyzing drums found in the woods or in a dump. It is a fourth objective of the invention that it be useable for collecting multiple samples in a waste burial area or a field of 55 gallon or other conventional drums. These and other objectives may be met using tubular chambers, each chamber being separated axially from each other by a tubular flexible material, with the top and bottom chambers being attached to a handle. A middle chamber being the sample collection chamber is attached radially to a shaft which is rotationally operable by the user to form a pair of iris valves at the top and bottom of the sample chamber which secure the sample for removal.

BRIEF DESCRIPTION OF THE DRAWINGS

FIG. 1 is a lateral view of the sampling device.
FIG. 2 shows the tubular chambers in the open position.
FIG. 3 shows the tubular chambers in the closed position.

DETAILED DESCRIPTION OF THE INVENTION

Figure 4:
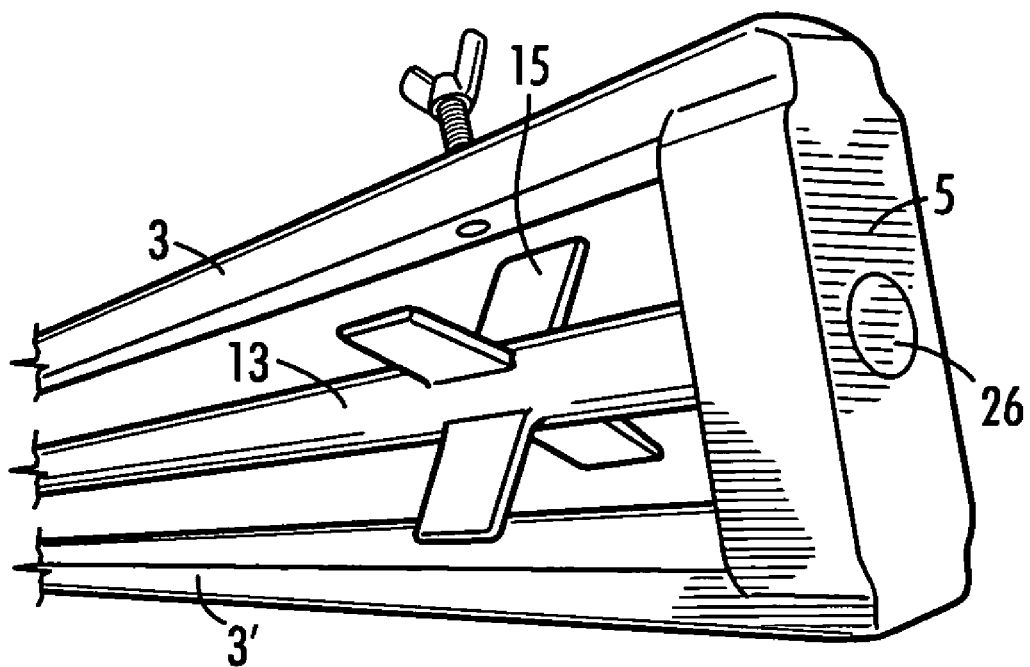
FIG. 4 shows the handle, frame and valve-operating mechanism.
Figure 5:
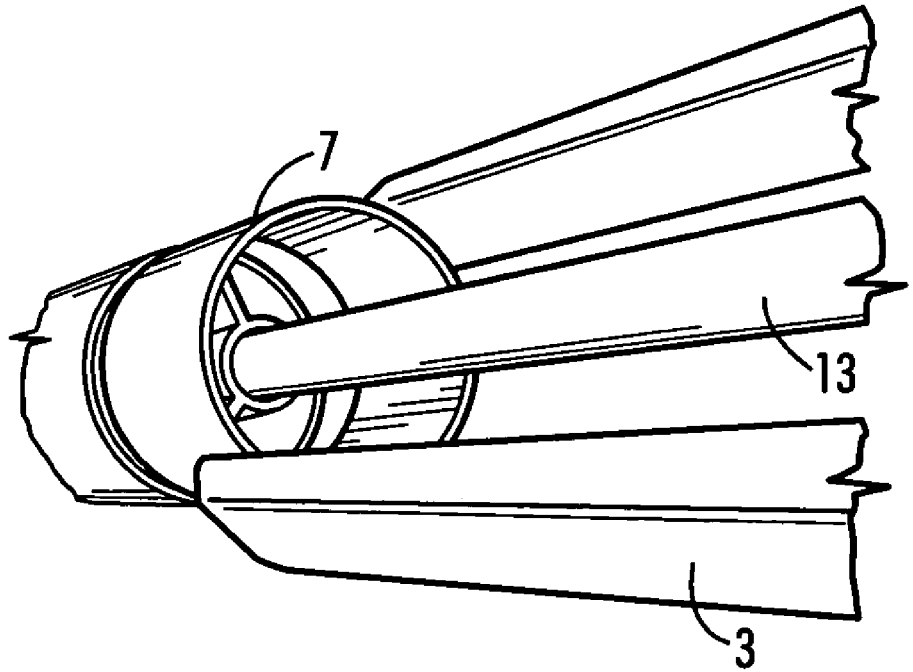
FIG. 5 shows the relationship of frame and valve-operating mechanism to the tubular chambers.

The sampling device 1 has a frame 3, shown in FIG. 1 as a pair of parallel rods 3, 3' crossed at the proximal end by a handle 5 and secured to a top tabular chamber 7 at the distal end. A tube 13, mounted on a shaft 26, having rotating means 15 passes through the tubular chamber 7, and attaches to a sampling chamber 9. The shaft 26 extends from its attachment to the upper frame 5, through the center of the rotating tube 13 and attaches to the bottom chamber 11. Chambers 9 and 11 are suspended by a plurality of radial vanes, shown in FIGS. 6 and 7 as element 25. Sampling chamber 9 is rotated using rotating means tube 13. Boring chamber 11 and chamber 7 are held stationary by shaft 26 and the parallel rods 3, 3' of the frame respectively. Flexible tubular connectors 21, 23 overlap the separations between chambers 7, 9, and 11. FIG. 2 illustrates the sample in the open position wherein the connectors appear as extensions of the chambers.

When tube 13 is rotated, sample chamber 9 is rotated relative to sample chambers 11 and 7, causing the flexible connectors 21 and 23 to pinch off in the manner of iris valves.

Figure 6:
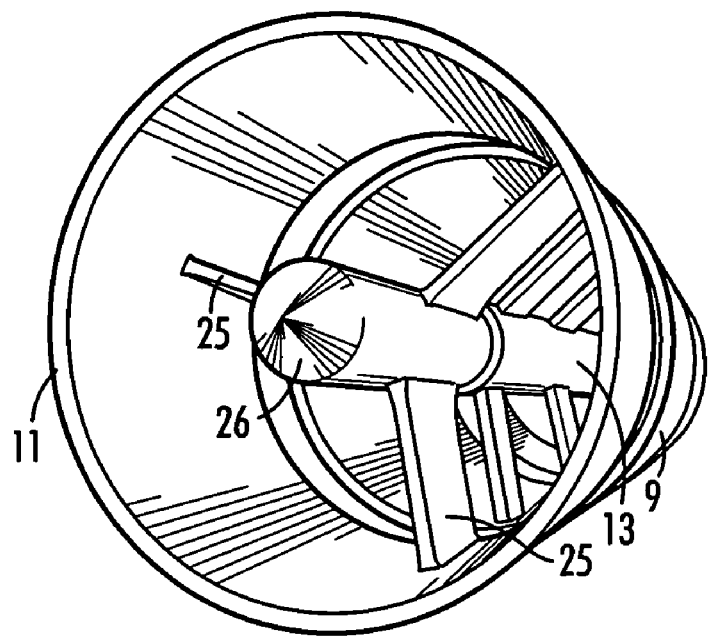
FIG. 6 is an upward view through the lower boring chamber with the sampling device in the open position.
Figure 7:
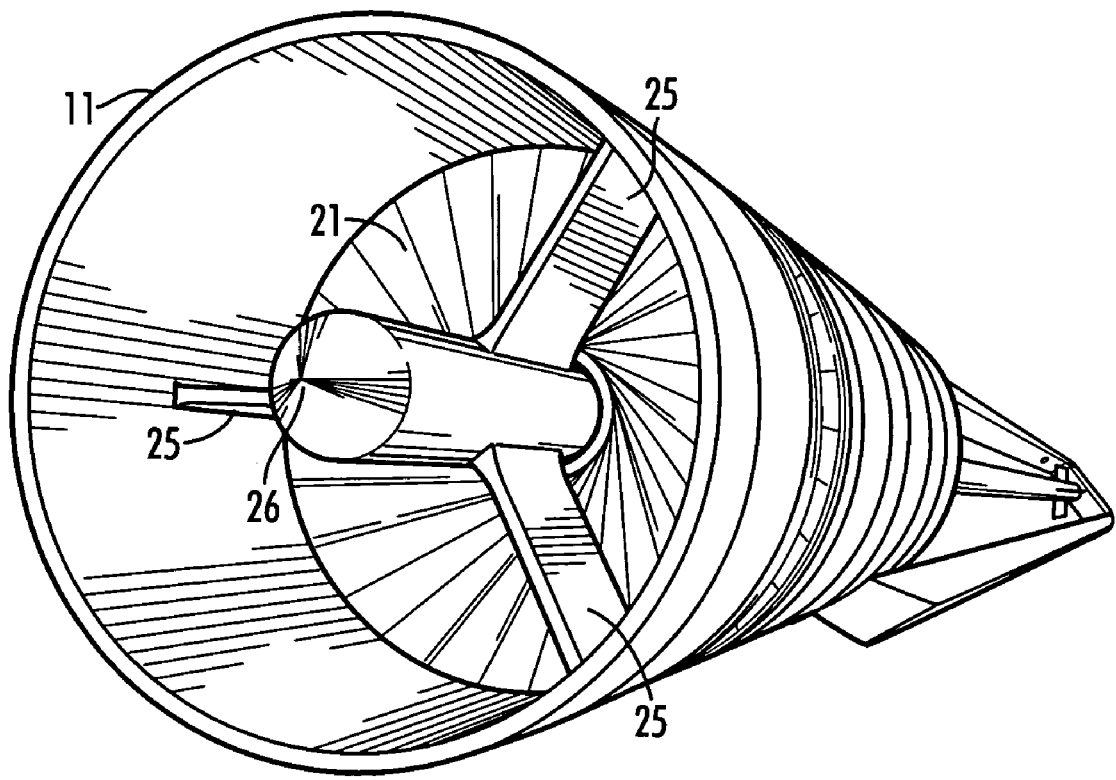
FIG. 7 is an upward view of the lower boring chamber with the sampling device in the closed position.

FIG. 4 shows details of the frame 3, handle 5 and rotating means 15. FIG. 6 shows the relationship of boring chamber 11 to sample chamber 9, tube 13 and stationary shaft 26. The radial supports 25 hold the chamber 11 stationary as the sample chamber 9 is rotated. FIG. 7 shows the result of the rotation as flexible connector 21 when it is closed in the manner of an iris valve.

Material of construction of the sampler of this invention depend upon size and expected use. Al alloys are suitably light and inert for most uses in non-corrosive environments. Brass or bronze is appropriate where sparking is a problem, such as an area with flammable solvents. Monel®, Hastelloys® and Inconel® may be chosen for specific situations. Engineering plastics, especially reinforced plastics, are useful in corrosive environments. Ferrous metals, especially stainless steel, are also suitable.

The flexible tubular connectors are chosen likewise for the expected use. Almost any material not attacked by water or petroleum is suitable provided it is available in a thickness sufficiently thin to form an iris valve without excessive torque. Fabric or fibrous reinforcement is preferred for most polymeric material.

In addition to sampling of silt and sludge, the sampler of this invention may be used for grab sample of powders and grains and any collection of materials which can be penetrated without excessive force and cut cleanly by the iris valve.

INDUSTRIAL UTILITY

The sampler of this invention is useful for obtaining depth-specific samples in soft environments such as silt, sand, sludge and pulverized materials. The small size allows easy access to drums, tanks, silos and other containment devices. The samples may be collected for process control, environmental control or research.

The invention has been described in terms of preferred embodiments. Additions and modifications apparent to those with skill in the art are subsumed within the scope of the invention.

We claim:

1. A sampling device comprising:
   a) a rigid frame (3) having a handle (5) attached to a stationary shaft (26);
   b) a plurality of tubular chambers connected to said frame distal to said handle; said plurality of tubular chambers comprising an upper tubular chamber (7), a middle tubular sample chamber (9), and a stationary tubular lower boring chamber (11)
   c) a rotatable tube (13) mounted on said stationary shaft having a first end rotatably mounted in said handle and passing through an end key and said upper tubular chamber (7);
   d) said middle tubular sample chamber (9) supported by said rotatable tube (13);
   e) said stationary tubular lower boring chamber (11) supported by said stationary shaft; and
   f) a pair of flexible connectors (21, 23) located to engage one end of said stationary upper chamber, both ends of said middle tubular sample chamber, and one end of said stationary tubular lower boring chamber.

2. A sampling device according to claim 1 wherein said flexible tubular connectors function as iris valves.

3. A sampling device according to claim 2 wherein said flexible tubular connectors are formed from a deformable sheet polymeric material.

4. A sampling device according to claim 3 wherein said deformable polymeric material is supported by a fibrous material.

5. A sampling device according to claim 1 wherein the structure is formed from a material selected from the group consisting of Al, brass, bronze, engineering plastics, ferrous metals and engineering plastics.

* * * * *